United States Patent
Gust et al.

(10) Patent No.: US 10,590,432 B2
(45) Date of Patent: Mar. 17, 2020

(54) PLANTS HAVING INCREASED RESISTANCE TO PATHOGENS AND METHOD FOR PRODUCING SAID PLANTS

(71) Applicant: Eberhard Karls Universität Tübingen, Tübingen (DE)

(72) Inventors: Andrea Gust, Ammerbuch (DE); Malou Fraiture, Rameldange (LU); Weiguo Zhang, Zurich (CH); Frédéric Brunner, Freising (DE)

(73) Assignee: EBERHARD KARLS UNIVERSITÄT TÜBINGEN, Tübingen (DE)

( * ) Notice: Subject to any disclaimer, the term of this patent is extended or adjusted under 35 U.S.C. 154(b) by 196 days.

(21) Appl. No.: 14/895,548

(22) PCT Filed: Jun. 5, 2014

(86) PCT No.: PCT/DE2014/000287
§ 371 (c)(1),
(2) Date: Dec. 3, 2015

(87) PCT Pub. No.: WO2014/194882
PCT Pub. Date: Dec. 11, 2014

(65) Prior Publication Data
US 2016/0122779 A1    May 5, 2016

(30) Foreign Application Priority Data
Jun. 8, 2013  (DE) .......................... 10 2013 009 665

(51) Int. Cl.
*C12N 15/82*    (2006.01)
*C07K 14/415*   (2006.01)

(52) U.S. Cl.
CPC ........ *C12N 15/8282* (2013.01); *C07K 14/415* (2013.01); *C12N 15/8279* (2013.01); *C12N 15/8281* (2013.01)

(58) Field of Classification Search
CPC .............. C07K 14/415; C12N 15/8282; C12N 15/8281
See application file for complete search history.

(56) References Cited

PUBLICATIONS

Schmid, Markus, et al. "A gene expression map of *Arabidopsis thaliana* development." Nature genetics 37.5 (2005): 501.*
Zipfel, Cyril, et al. "Bacterial disease resistance in *Arabidopsis* through flagellin perception." Nature 428.6984 (2004): 764-7.*
Pearson, William R. "An introduction to sequence similarity ("homology") searching." Current protocols in bioinformatics (2013): 3-1.*
Zipfel, Cyril. "Plant pattern-recognition receptors." Trends in immunology 35.7 (2014): 345-351.*
Gao, Minghui, et al. "Regulation of cell death and innate immunity by two receptor-like kinases in *Arabidopsis*." Cell host & microbe 6.1 (2009): 34-44.*
Wang, Guodong, et al. "A genome-wide functional investigation into the roles of receptor-like proteins in *Arabidopsis*." Plant physiology 147.2 (2008): 503-517.*
Schmid, Markus, et al. "A gene expression map of *Arabidopsis thaliana* development." Nature genetics 37.5 (2005): 501 (Year: 2005).*
Zipfel, Cyril, et al. "Bacterial disease resistance in *Arabidopsis* through flagellin perception." Nature 428.6984 (2004): 764-7 (Year: 2004).*
Shiu, Shin-Han, et al. "Comparative analysis of the receptor-like kinase family in *Arabidopsis* and rice." The plant cell 16.5 (2004): 1220-1234. (Year: 2004).*
Gao, Minghui, et al. "Regulation of cell death and innate immunity by two receptor-like kinases in *Arabidopsis*." Cell host & microbe 6.1 (2009): 34-44. (Year: 2009).*
Wang, Guodong, et al. "A genome-wide functional investigation into the roles of receptor-like proteins in *Arabidopsis*." Plant physiology 147.2 (2008): 503-517. (Year: 2008).*
Ma, Lisong, and M. Hossein Borhan. "The receptor-like kinase SOBIR1 interacts with *Brassica napus* LepR3 and is required for *Leptosphaeria maculans* AvrLm1-triggered immunity." Frontiers in plant science 6 (2015): 933 (Year: 2015).*
Zipfel, Cyril. "Plant pattern-recognition receptors." Trends in immunology 35.7 (2014): 345-351 (Year: 2014).*
Jiang, Zhengning, et al. "RLP1. 1, a novel wheat receptor-like protein gene, is involved in the defence response against *Puccinia striiformis* f. sp. *tritici*." Journal of experimental botany 64.12 (2013): 3735-3746 (Year: 2013).*
Liebrand, Thomas WH, et al. "Receptor-like kinase SOBIR1/EVR interacts with receptor-like proteins in plant immunity against fungal infection." Proceedings of the National Academy of Sciences 110.24 (2013): 10010-10015 (Year: 2013).*

(Continued)

*Primary Examiner* — Weihua Fan
(74) *Attorney, Agent, or Firm* — Nixon Peabody LLP; Mark J. FitzGerald; Nicole D. Kling

(57) ABSTRACT

The invention relates to a plant having increased resistance to pathogens, wherein the protein SOBIR1 from *Arabidopsis thaliana* or a homologous protein, which is capable of interacting with at least one of the PRR receptor proteins RLP30 or RLP1, and at least one of the PRR receptor proteins RLP30 or RLP1 are overexpressed in comparison with the wild-type plant or are newly synthesized. The pathogens are preferably fungi, in particular from the genus *Sclerotinia*, and bacteria, in particular from the genus *Xanthomonas*. The invention further relates to a method for producing a plant having increased resistance to pathogens.

8 Claims, 3 Drawing Sheets

(56) References Cited

PUBLICATIONS

Figure 1:
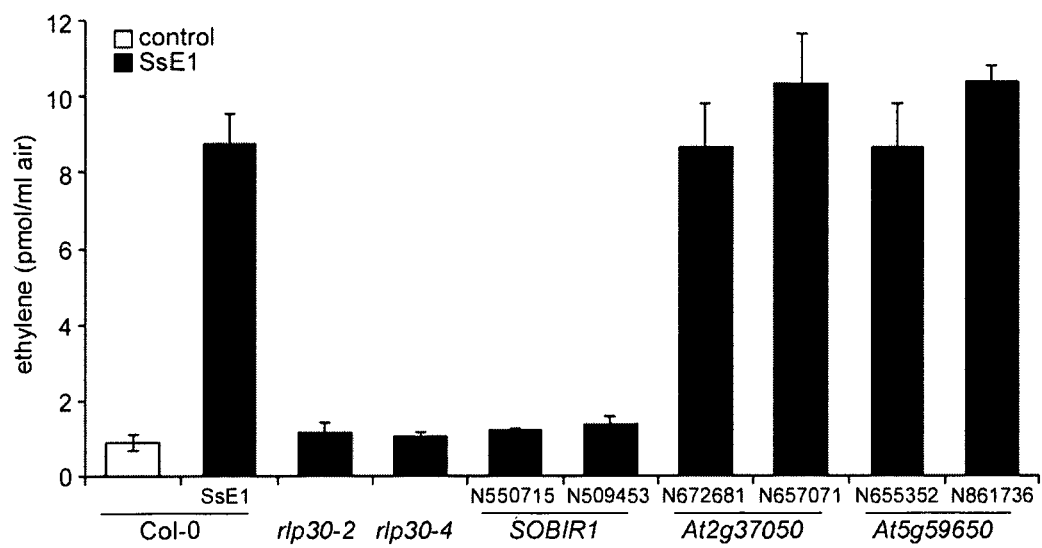

Shiu, Shin-Han, et al. "Comparative analysis of the receptor-like kinase family in *Arabidopsis* and rice." The plant cell 16.5 (2004): 1220-1234. (Year: 2004).*

Gao, Minghui, et al. "Regulation of cell death and innate immunity by two receptor-like kinases in *Arabidopsis*." Cell host & microbe 6.1 (2009): 34-44. (Year: 2009).*

Wang, Guodong, et al. "A genome-wide functional investigation into the roles of receptor-like proteins in *Arabidopsis*." Plant physiology 147.2 (2008): 503-517. (Year: 2008).*

Gao, M., et al., "Regulation of Cell Death and Innate Immunity by Two Receptor-like Kinases in *Arabidopsis*," *Cell Host & Microbe*, 6:33-44, (Jul. 23, 2009).

Leslie, M.E., et al., "The EVERSHED Receptor-Like Kinase Modulates Floral Organ Shedding in *Arabidopsis*," *Development Biology*, 137:67-476, (2010).

Leslie, M.E., et al., "The EVERSHED Receptor-Like Kinase Modulates Floral Organ Shedding in *Arabidopsis*," *Development Biology*, 331:p. 409, Program/Abstract #68, (Jul. 15, 2009).

Jehle, A.K., et al., "The Receptor-Like Protein ReMAX of *Arabidopsis* Detects the Microbe-Associated Molecular Pattern eMax from Xanthomonas," *The Plant Cell Online*, 25:2330-2340, (Jun. 2013).

Liebrand, T.W.H., et al., "Receptor-Like Kinase SOBIR1/EVR Interacts With Receptor-Like Proteins in Plant Immunity Against Fungal Infection," *PNAS* 110(24):10010-10015, (May 28, 2013).

Wang, G., et al., "A Genome-Wide Functional Investigation Into the Roles of Receptor-Like Proteins in *Arabidopsis*," *Plant Physiology*, 147:503-517, (Apr. 23, 2008). Date on ISR of PCT/DE2014/000287 is Apr. 11, 2008, which differs from this citation.

Zhang, W., et al., "*Arabidopsis* Receptor-Like Protein30 and Receptor-Like Kinase Suppressor of BIR1-1/Evershed Mediate Innate Immunity to Necrotrophic Fungi," *The Plant Cell*, 25:4227-4241, (Oct. 2013).

Zhang, W., "Identification and Characterization of the Novel Fungal MAMP SsE1 and its Receptor-Like Protein (RLP30)-Based Perception System in *Arabidopsis*," thesis, Nov. 26, 2013, XP055147668, retrieved from the Internet: URL: https://publikationen.uni-tuebingen.de/xmlui/bitstream/handle/10900/49988/pdf/Thesis_Weiguo_Zhang.pdf?sequence=1&isAllowed=y.

International Search Report from PCT/DE2014/000287 (entitled, "Plants Having Increased Resistance to Pathogens and Method for Producing Said Plants"), dated Oct. 29, 2014.

International Preliminary Report on Patentability from PCT/DE2014/000287 (entitled, "Plants Having Increased Resistance to Pathogens and Method for Producing Said Plants"), dated Dec. 8, 2015.

* cited by examiner

PLANTS HAVING INCREASED RESISTANCE TO PATHOGENS AND METHOD FOR PRODUCING SAID PLANTS

RELATED APPLICATION(S)

This application is the U.S. National Stage of International Application No. PCT/DE2014/000287, filed on Jun. 5, 2014, which designates the U.S., published in German, and claims priority under 35 U.S.C. §§ 119 or 365(c) to DE Application No.10 2013 009 665.0, filed Jun. 8, 2013. The entire teachings of the above application(s) are incorporated herein by reference.

The present invention relates to plants, especially agricultural plants, with increased resistance against pathogens as well as to processes for their preparation.

Plants are constantly exposed to a risk of contamination by pathogens. Plant diseases caused by pathogenic organisms can result in a complete loss of a harvest of agricultural crop plants. A conventional method for tackling plant diseases is the use of chemical pesticides. However, these measures will typically also result in the loss of a portion of the harvest.

The use of chemical pesticides for agricultural crop plants can have negative effects on humans as well as the environment. Furthermore, these measures are very costly and labor intensive. Moreover, pathogens that are subjected to a treatment with chemical pesticides often develop adaptation mechanisms. Therefore, these measures often do not achieve the desired protective effect.

An alternative to the use of chemical agents is the use of disease-resistant varieties. However, the breeding of pathogen-resistant varieties using classical breeding methods is very time consuming and challenging due to the in some cases very complex genomes of agricultural crop plants. For the development of targeted and effective plant protection measures new strategies and technologies are therefore needed.

Plants have a natural immunity providing an effective defense against pathogens. A better understanding of the molecular basis of this natural immunity could contribute to the development of new plant protection measures.

The majority of pathogens are detected by the plant via so called pathogen-associated molecular patterns (PAMPs, also MAMPs—called microbe-associated molecular patterns). These are structural motifs or molecules that are characteristic for a broad spectrum of microorganisms, and which allow a plant to detect the intrusion of pathogens. In general, these structural motifs are essential for a microorganism and highly conserved. PAMPs are recognized by the corresponding pattern recognition receptors (PRRs) which as one part of the natural immunity form the basis for a broad-spectrum resistance in plants against pathogens.

The model plant thale cress (*Arabidopsis thaliana*), as well as other higher plants, has a large number of surface receptor proteins which play an important role in both constitutive ("congenital") as well as adaptive processes, such as growth regulation, development, organogenesis and responses to external stimuli.

The largest family of surface receptor proteins in *A. thaliana* are the so called receptor-like kinase proteins (RLK), which are encoded by more than 600 different genes. These are transmembrane proteins, composed of a cytoplasmic domain, which exerts a kinase function during intracellular signal transduction, a transmembrane domain, and an extracellular domain, which is responsible for ligand binding. Many RLK proteins harbor a region with so called leucine-rich repeats (LRR) that can recognize and bind specific PAMPs from pathogenic organisms and which thus are involved in the defense against pathogens in plants.

SOBIR1 is a LRR-RLK protein and consists of four extracellular LRRs, a single transmembrane domain and a cytoplasmic serine-threonine protein kinase domain. Previously it was shown that SOBIR1 overexpression can activate cell death in plants, probably in conjunction with the protein BIR1 (Gao et al., 2009, Cell Host & Microbe 6, 34-44). There are also indications that SOBIR1 has a function as an inhibitor of abscission (Leslie et al., 20 10, Development 137, 467-476), being primarily responsible for plant development, but which is not of importance for the resistance to pathogens.

Also, representatives of the so-called family of receptor-like proteins (RLP) are known to play a role in mediating plant immunity. The structure of RLP proteins is similar to the structure of RLK proteins, with the difference that they lack the cytoplasmic kinase domain (Wang G, et al, 2008, Plant Physiol 147 (2):. 503-517). Known representatives of this group are for example the proteins LeEix1 and LeEix2 from tomato plants. These proteins recognize the so called cell wall-derived ethylene-inducing xylanase (Eix) from the fungus *Trichoderma* (Ron M & A Avni, 2004, Plant Cell 16 (6): 1604-1615). Also, the RLP protein Ve1, which recognizes the protein Ave1 from different fungal species belongs to this class (de Jonge R, et al, 2012 Proc Natl Acad Sci USA 109 (13):. 5110-51 15).

Recently it was shown that the RLP proteins Cf-4, Cf-2.2, Cf-4E, Cf-9, Peru2 (mediates immunity against *Cladosporium fulvum*) and Ve1 (mediates immunity against *Verticillium dahliae*) are involved in the defense against pathogens in plants of the genera *Solanum* and *Nicotiana* by interacting with the protein SOBIR1 (Liebrand et al, 2013, Proc Natl Acad Sci USA, 1 10 (24):. 10010-5). SOBIR1 also interacts with the RLPs EIX2 (mediates response to the elicitor "ethylene-inducing xylanase" from *Trichoderma viride*), CLV2 (mediates meristem and organ development) and TMM (mediates stomatal development). All tested immune-associated RLP proteins in Liebrand et al. are endogeneous proteins of plants of the family Solanaceae and mediate immunity against pathogens (eg. *C. fulvum* and *V. dahliae*), against which these plants can mount an immune response naturally. Solutions for generating resistance to other pathogens against which no endogeneous immunity is mounted by the plants were not suggested by Liebrand et al.

The object of the present invention is therefore to provide plants with increased resistance against specific pathogens, and a method for producing such plants.

This object is achieved by providing a plant, in which the protein SOBIR1 of *Arabidopsis thaliana* (Gao et al, 2009, Cell Host & Microbe 6, 34, 44; Leslie et al, 2010 Development 137, 467-476), or a homologous protein which is capable of interacting with at least one of the PRR receptor proteins RLP30 or RLP1, and at least one of the PRR receptor proteins RLP30 or RLP1, are overexpressed compared to the wild-type plant, or are newly synthesized.

In the present invention it could be shown that the protein SOBIR1 interacts with proteins from the PRR-protein-family, in particular with RLPs, and is necessary for the localization of these proteins in the plasma membrane, in particular for inducing an immune response in plants in conjunction with PRR proteins is (see examples).

Particularly preferred is that the proteins SOBIR1 and RLP are heterologously expressed in plant species which lack the corresponding SOBIR1/RLP-protein complex.

RLP30 is necessary in *A. thaliana* for resistance to fungi. In particular RLP30 recognizes SsE1 from the pathogenic fungus *Sclerotinia sclerotiorum* and is therefore involved in the immune defense against fungal pathogens having this PAMP. As shown in the present invention for the first time, the protein SOBIR1 is required for the development of resistance in addition to RLP30. Some plant families lack this receptor complex, for example the representatives of the Solanaceae family, as demonstrated in the present invention. For this reason, these plants do not recognize SsE1, so that they do not successfully fight off an infection caused by this fungal species. A heterologous expression of the proteins SOBIR1 and RLP30 will in accordance with the invention establish, or increase, the resistance to pathogenic fungi in such plants.

In addition, the data produced in context of the present invention indicate that SOBIR1 together with another RLP protein—RLP1—is involved in the immune defense in plants. From RLP1 is known that it recognizes and binds EMAX (enigmatic microbe-associated molecular pattern of *Xanthomonas*) in *A. thaliana* (Jehle et al., 2013, Plant Cell 25, 2330-2340). Thus SOBIR1 seems also to be involved in the immune defense against pathogenic bacteria. A co-expression of SOBIR1 and RLP1 will increase the resistance to pathogenic bacteria in accordance with the present invention.

Furthermore, the invention relates to a method for producing a plant with increased resistance to pathogens. In this method the protein SOBIR1 of *A. thaliana*, or a homologous protein which is capable of interacting with at least one of the PRR receptor proteins RLP30 or RLP1, and at least one of the PRR receptor proteins RLP30 or RLP1, are overexpressed compared to the wild-type plant, or are newly synthesized.

The expression of the proteins can be modulated by conventional methods known to the skilled person. Possible methods include ectopic expression, in particular a heterologous expression, or mutagenesis, RNA interference, DNA methylation or other molecular biology methods.

Further advantages, features and possible applications of the invention are described in the following by the below-described examples with reference to the figures.

FIG. 1: Ethylene response to SSE1 in sobir1-mutants compared to other RLK-mutants.

Leaf discs of 5-week-old *Arabidopsis* plants were not treated as a control (control) or treated with a partially purified extract of *S. sclerotioum* (SsE1). After three hours of incubation, the production of ethylene was measured by gas chromatography. In each case two independent T-DNA insertion lines-were tested; two rlp30 mutants were used as positive control. Shown are the mean values of two experiments±SD FIG. 2: SOBIR1 and RLP30 interact directly.

In *N. benthamiana* leaves constructs for SOBIR1-HA and RLP30-GFP were transiently expressed. Total protein from leaves (input) was subjected to an immune-precipitation with anti-HA agarose beads, followed by immunoblot analysis with anti-GFP antibodies (detect RLP30-GFP), or anti-HA antibodies (detect SOBIR1-HA).

Figure 3:
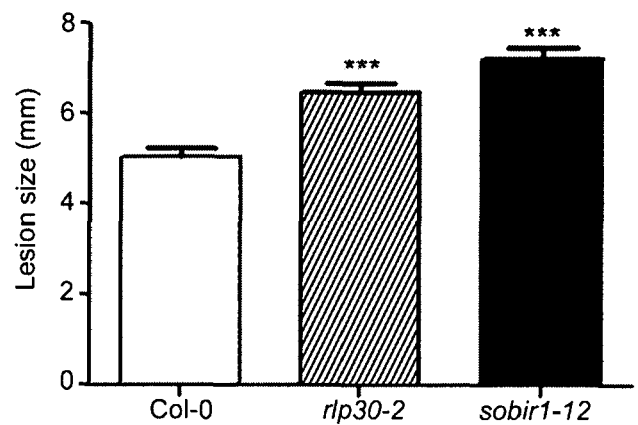

FIG. 3: SOBIR1 is necessary for resistance to fungal pathogens.

Col-0 wild type plants or rlp30 and sobir1 mutants were infected with *B. cinerea* spores (5 µl drop of a 2×10$^6$ pores ml$^{-1}$ solution) and the lesion sizes were determined after 3 days. Shown are mean values (n=2)±S.E.M. (n=20). Stars show significant differences when compared to Col-0 ((***P<0.005, Student's t-test).

Figure 4:
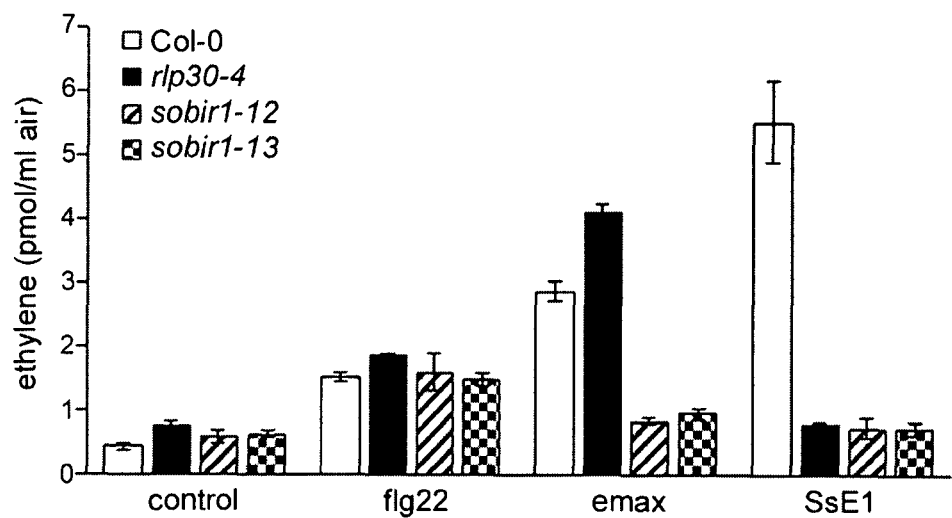

FIG. 4: sobir1 mutants are limited in the recognition of SsE1 and emax.

Figure 5:
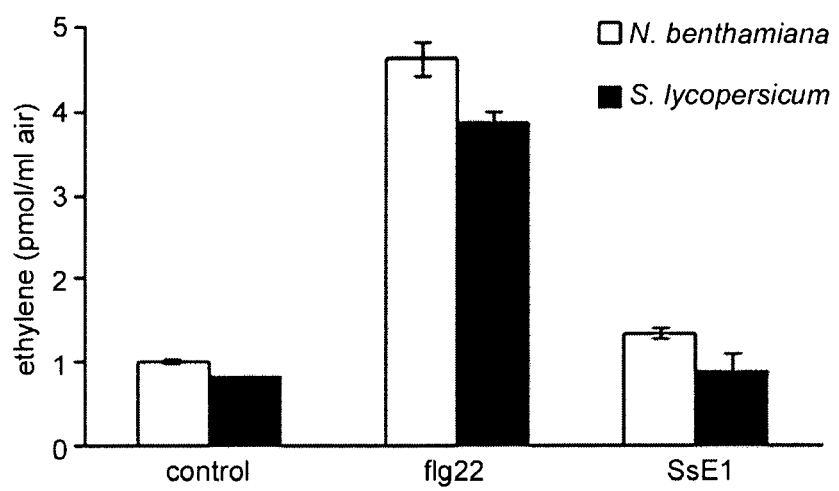

Leaf discs of 5-week-old *Arabidopsis* plants were not treated (control) or treated with 500 nM flg22, or partially purified extracts from *S. sclerotiorum* (SsE1) or *Xanthomonas axonopodis* pv. *Citri* (emax). After three hours of incubation, the production of ethylene was measured using gas chromatography. Shown are the mean values of two measurements±SD FIG. 5: The SsE1-recognition system does not exist in Solanaceae.

Leaf discs of *Nicotiana benthamiana* or *Solanum lycopersicum* were treated with SsE1 or 500 nM flg22 and after 3 hours the ethylene production was measured by gas chromatography. Shown are the mean values of two measurements±SD FIG. 6: Co-expression of RLP30 and SOBIR1 conveys SsE1 response in *N benthamiana*.

In *N. benthamiana*-leaves constructs for SOBIR1-HA and RLP30-GFP were each transiently expressed alone or in combination. 2 days after *Agrobacterium* infiltration, leaf pieces were treated with either *S. sclerotiorum*-extract (SsE1) or 500 nM flg22, or as a control, were left untreated (−). Ethylene production was measured by gas chromatography after 3 hours. Shown are the mean values of two measurements±SD

EXAMPLES

Identifying SOBIR1 as an Interaction Partner for RLP30

Looking for a potential interaction partner of RLP30, the latter being involved in signal transduction during infection by a pathogen, existing databases were searched for membrane protein interactions. In a yeast-two-hybrid database (http://www.assoociomics.org/Associomics/Home.html) the following RLKs were identified out of a total of 66 potential interaction partners that interact with RLP30:

| AGI ID | Functional Description |
| --- | --- |
| AT1G21240 | WAK3, wall associated kinase 3 RLK/Pelle |
| AT2G31880 | SOBIR1, EVR, Leucine-rich repeat protein kinase family protein |
| AT2G37050 | Leucine-rich repeat protein kinase family protein |
| AT4G20790 | Leucine-rich repeat protein kinase family protein |
| AT5G59650 | Leucine-rich repeat protein kinase family protein |

For three of five RLKs which interact with RLP30, T-DNA insertion lines were obtained from the Nottingham-*Arabidopsis* Stock Centre (NASC) and tested for SsE1-triggered ethylene production. Only the sobir1 mutants (Suppressor of BIR1-1, At2g31880, also known as EVR, Evershed) did not show SsE1-induced ethylene production, while the T-DNA insertion lines of the other-RLKs showed a normal response to SsE1 (FIG. 1).

Figure 2:
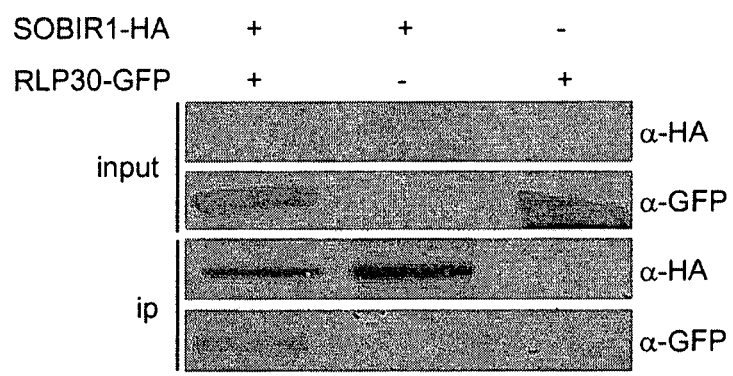

With the aid of *Agrobacterium*-mediated transient co-expression of epitope-tagged SOBIR1 and RLP30 constructs in *Nicotiana benthamiana*, it could be shown that SOBIR1 physically interacts with RLP30, in a ligand-independent manner (FIG. 2). For this SOBIR1-HA (HA-epitope tag at the C-terminus) was expressed together with RLP30-GFP (GFP-epitope tag at the C-terminus) in leaves of about 3-week-old *N. benthamiana* plants. After two days, protein extracts were produced from the leaves. From these protein extracts, SOBIR1-HA was immuno-precipitated (anti-HA agarose) and the presence of both RLP30-GFP (GFP antibodies) and SOBIR1-HA (HA antibody) was tested by Western blot analysis. Here SOBIR1-HA has been identified to be in a complex with RLP30-GFP, in the absence of SsE1 (FIG. 2).

In addition, resistance of sobir1 mutants against infections with the neurotrophic fungus *B. cinerea* was investigated. It was found that similar to rlp30 mutants also sobir1 mutants were hyper susceptible and displayed an increased lesion diameter after infection with *Botrytis* (FIG. 3). For plant infection the *B. cinerea* isolate B05-10 was grown on synthetic medium. The leaf infection of 4-5 week old *Arabidopsis* plants was performed as described by Kemmerling et al. (2007, Current Biology). For the quantification of fungal DNA, four leaves infected with *B. cinerea* were harvested per genotype (day 2 or 3 of infection) by freezing. The samples were ground to a powder under liquid nitrogen and total DNA was isolated with CTAB buffer (1, 4 M NaCl, 20 mM EDTA (pH 8), 100 mM Tris-HCl (pH 8), 2% CTAB). Fungal biomass was determined by quantitative real-time PLCR using the SYBR Green qPCR Master Mix (Fermentas). The relative content of genomic DNA of the actin gene of *Botrytis* and the genomic DNA of the *Arabidopsis* Rubisco gene (large subunit) were used to quantify fungal biomass (Fradin et al., 2011).

Identifying SOBIR 1 as an Interaction Partner for RLP1

Interestingly, it was observed that SOBIR1 is also involved in the recently published recognition of the *Xanthomonas*-elicitor EMAX via RLP1. Gene inactivation of SOBIR1 in *Arabidopsis* plants resulted in a lack of ethylene response to Emax treatment, similar to the situation after a treatment with SsE1 (FIG. 4). In contrast, rlp30 mutants responded normally to EMAX, which suggests that the specificity of the recognition of SsE1 and EMAX depends on the respective RLP.

Heterologous Co-expression of SOBIR1 and RLP30 in Solanaceae

Figure 6:
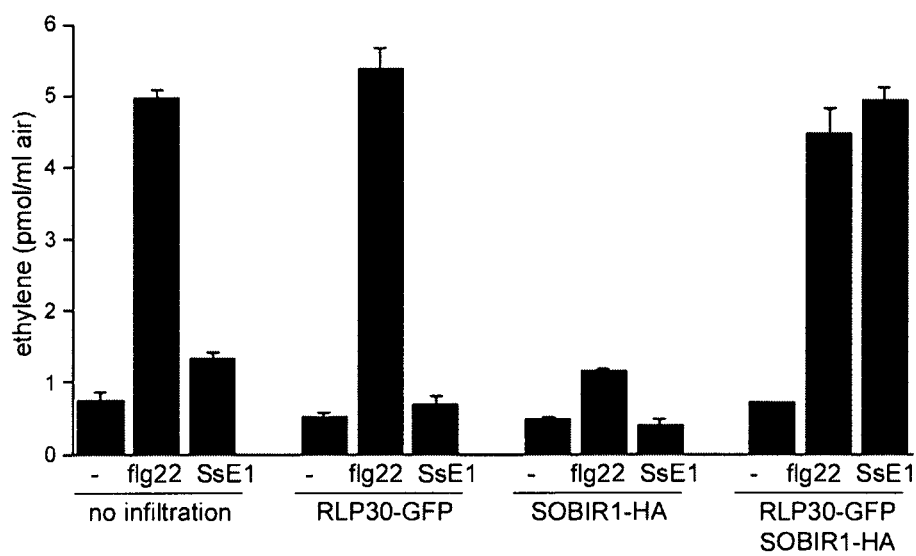

In tobacco (*N. benthamiana*) and tomato (*S. lycopersicum*) SsE1, unlike the 22 amino acid peptide flg22 of flagellin, could not induce the production of ethylene (FIG. 5), which indicates that the detection of SsE1 is *Arabidopsis*-specific. With the aid of *Agrobacterium*-mediated transient co-expression of epitope-tagged SOBIR1 and RLP30 constructs in *Nicotiana*, it could be shown that when both proteins are expressed together, SsE1 induced ethylene production can also be triggered in tobacco. The expression of the individual components (SOBIR1 alone or RLP30 alone) does not lead to an SsE1 response. For this purpose, SOBIR1-HA (HA-epitope tag at the C terminus) or RLP30-GFP (GFP-epitope tag at the C terminus) were expressed each alone or in combination in leaves of about 3-week-old *N. benthamiana* plants, and the respective leaves were infiltrated with SsE1 (0.25 mg/ml) or flg22 (500 nM) after two days. Ethylene production was measured 3 hours after infiltration with the elicitor by gas chromatography (FIG. 6).

What is claimed is:

1. A plant with increased resistance to pathogens, in which the protein *Arabidopsis thaliana* Suppressor of BIR1-1 (AtSOBIR1) and at least one of the proteins *Arabidopsis thaliana* Receptor Like Protein 30 (AtRLP30) or *Arabidopsis thaliana* Receptor Like Protein 1 (AtRLP1), are newly synthesized by heterologous expression.

2. The plant according to claim 1, wherein the pathogens are fungi or bacteria.

3. A method for producing a plant with increased resistance to pathogens, comprising the step of overexpressing AtSOBIR1 and at least one of the proteins AtRLP30 or AtRLP1 in a plant compared to the wild-type plant by heterologous expression.

4. The method according to claim 3, wherein the overexpression is achieved by mutagenesis.

5. A genetically modified plant with increased resistance to *Sclerotinia* or *Xanthomonas*, in which a *Arabidopsis thaliana* protein Suppressor of BIR 1-1 (AtSOBIR1), and at least one of a *Arabidopsis thaliana* proteins Receptor Like Protein (AtRLP)30 or AtRLP1, are heterologously expressed, and wherein the plant is of a species that lacks a protein complex comprising homologs of AtSOBIR1 and AtRLP1 or AtSOBIR1 and AtRLP30.

6. The plant according to claim 2, wherein the fungi is of the genus *Sclerotinia*.

7. The plant according to claim 6, wherein the fungi of the genus *Sclerotinia* is a *Sclerotinia sclerotiorum* fungi.

8. The plant according to claim 2, wherein the bacteria is of the genus *Xanthomonas*.

* * * * *